United States Patent
Ishikawa et al.

(10) Patent No.: US 8,795,491 B2
(45) Date of Patent: Aug. 5, 2014

(54) METHOD OF PROCESSING SENSOR ELEMENT AND SENSOR ELEMENT

(75) Inventors: Tetsuya Ishikawa, Nagoya (JP); Sumiko Horisaka, Nagoya (JP); Yuji Okuda, Niwa-Gun (JP)

(73) Assignees: NGK Insulators, Ltd., Nagoya (JP); NGK Ceramic Device Co., Ltd., Komaki (JP)

( * ) Notice: Subject to any disclaimer, the term of this patent is extended or adjusted under 35 U.S.C. 154(b) by 114 days.

(21) Appl. No.: 13/040,621

(22) Filed: Mar. 4, 2011

(65) Prior Publication Data

US 2011/0240487 A1 Oct. 6, 2011

(30) Foreign Application Priority Data

Mar. 31, 2010 (JP) ................. 2010-081211
Jan. 28, 2011 (JP) ................. 2011-016199

(51) Int. Cl.
*G01N 27/26* (2006.01)

(52) U.S. Cl.
USPC .......... 204/426; 204/425; 204/427; 73/23.31; 73/23.32; 205/781; 205/784.5; 205/783.5; 205/785

(58) Field of Classification Search
USPC ................ 204/421–429; 73/23.31–23.32; 205/781, 783.5–785
See application file for complete search history.

(56) References Cited

U.S. PATENT DOCUMENTS

| 5,326,597 A | 7/1994 | Sawada et al. |
| 2002/0028367 A1* | 3/2002 | Sammes et al. ............ 429/31 |
| 2002/0038763 A1 | 4/2002 | E et al. |
| 2005/0126910 A1* | 6/2005 | Sakon et al. ............. 204/424 |
| 2005/0210657 A1* | 9/2005 | Nakagaki et al. ......... 29/592.1 |
| 2006/0089264 A1* | 4/2006 | Hong ..................... 505/100 |
| 2006/0151466 A1 | 7/2006 | Diehl |
| 2009/0205193 A1* | 8/2009 | Nakagaki et al. ......... 29/592.1 |

FOREIGN PATENT DOCUMENTS

| DE | 10 2004 060 291 | 6/2006 |
| EP | 1 180 681 | 2/2002 |
| EP | 2 058 653 | 5/2009 |
| WO | 2008/038773 A1 | 4/2008 |

* cited by examiner

*Primary Examiner* — Bach Dinh
(74) *Attorney, Agent, or Firm* — Burr & Brown, PLLC

(57) ABSTRACT

A method of processing a sensor element includes the steps of: (a) preparing a gas atmosphere containing hydrocarbon, having an air-fuel ratio of 0.80 to 0.9999, and having a small amount of oxidizing gas added thereto; and (b) subjecting a sensor element to a heat treatment in the gas atmosphere at a temperature of 500° C. or higher for 15 minutes or longer. The sensor element includes an electrochemical pumping cell constituted of an oxygen-ion conductive solid electrolyte and an electrode having a NOx reduction ability. A NOx gas in a measurement gas is reduced or decomposed in the electrode. A NOx concentration in the measurement gas is obtained based on a current which flows in the electrochemical pumping cell at a time of the reduction or decomposition.

6 Claims, 7 Drawing Sheets

F I G. 3
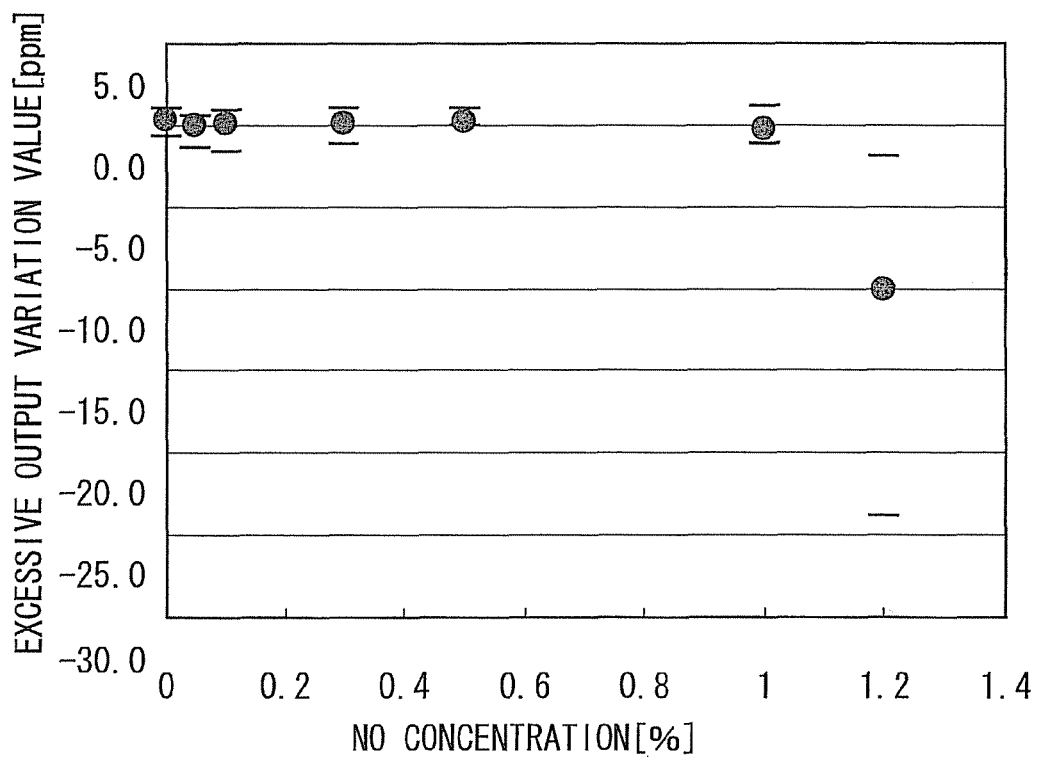

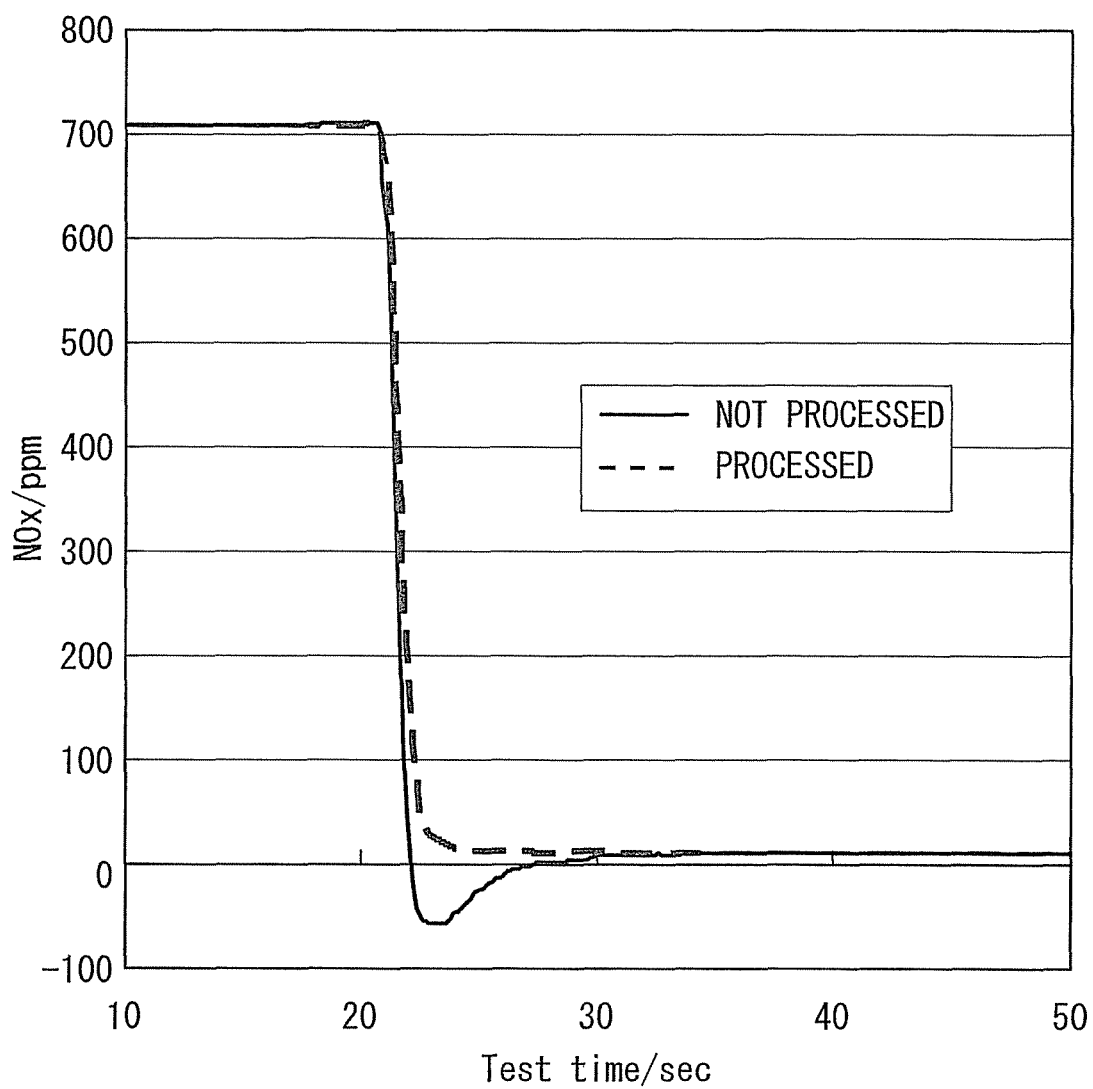
F I G . 4

F I G . 5
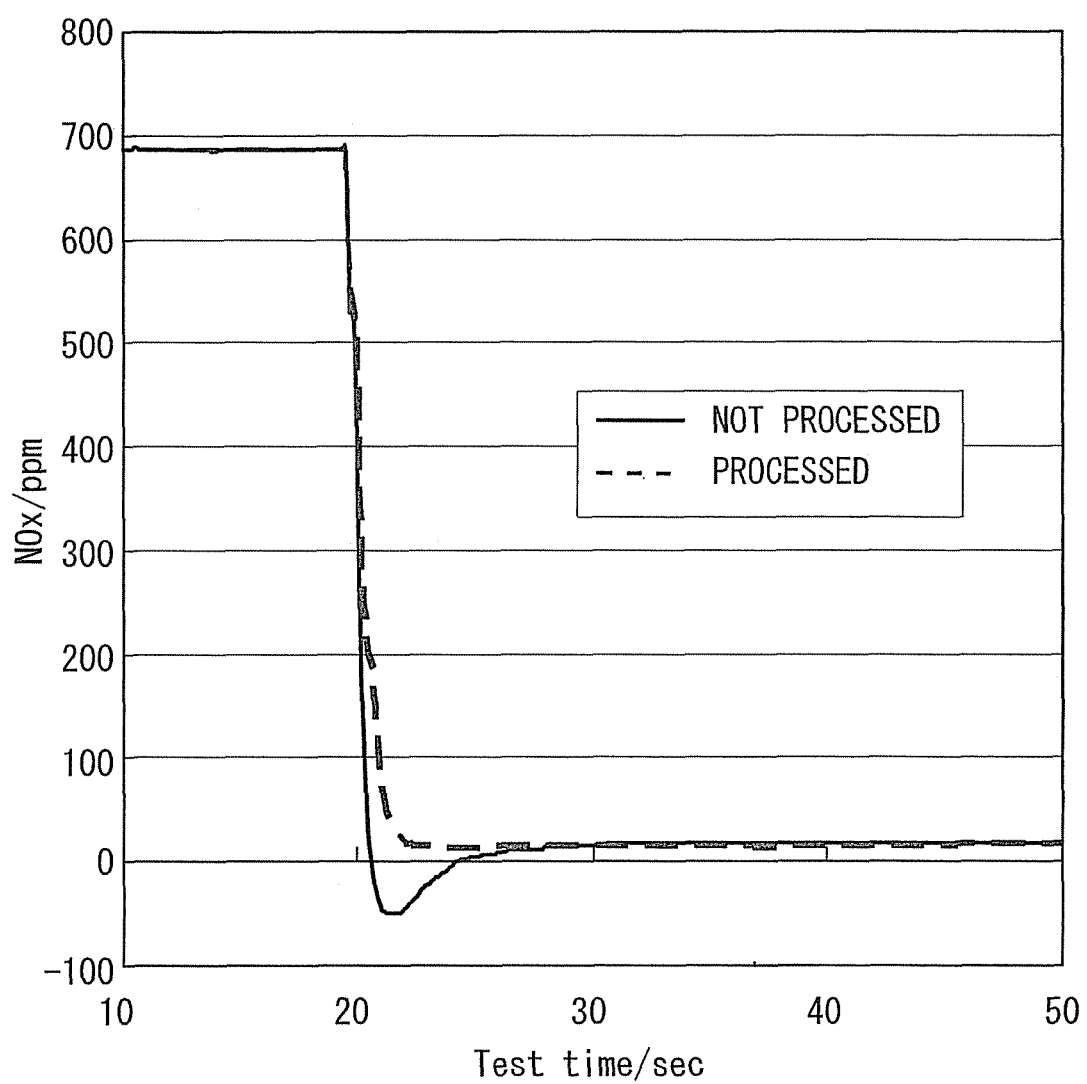

F I G . 6
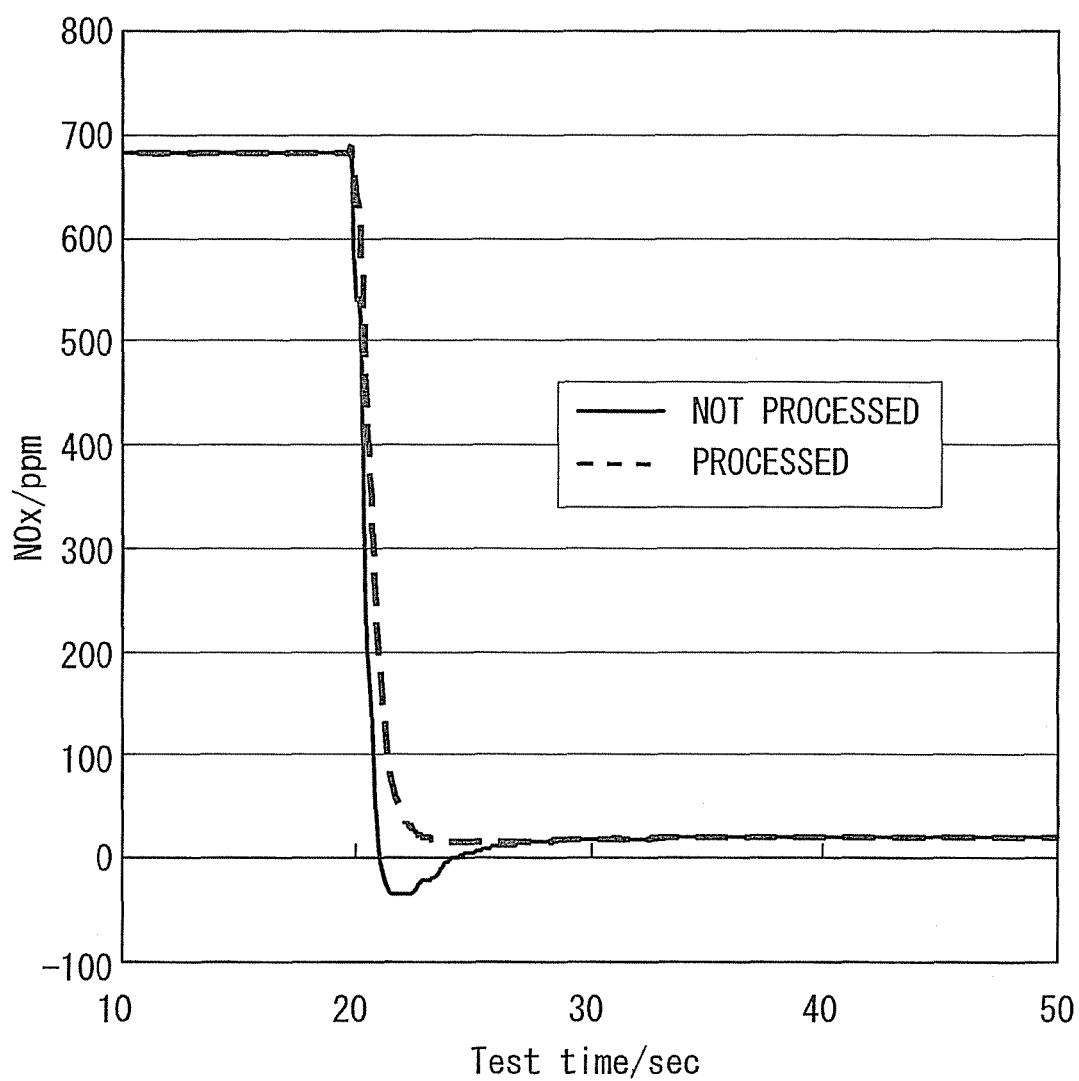

FIG. 7

|  | AIR-FUEL RATIO | TEMPERATURE (°C) | TIME (min) | APPEARANCE | EXCESSIVE OUTPUT VARIATION | INITIAL OUTPUT ($\mu$A) |
|---|---|---|---|---|---|---|
| EXAMPLE 4 | 0.750 | 700 | 120 | NG | NOT OBSERVED | -0.15 |
|  | 0.800 | 700 | 120 | OK | NOT OBSERVED | -0.03 |
|  | 0.900 | 700 | 120 | OK | NOT OBSERVED | -0.01 |
|  | 0.990 | 700 | 120 | OK | NOT OBSERVED | 0.02 |
|  | 0.9985 | 700 | 120 | OK | NOT OBSERVED | 0.03 |
|  | 0.999 | 700 | 120 | OK | NOT OBSERVED | 0.04 |
|  | 1.050 | 700 | 120 | OK | OBSERVED | 0.04 |
| EXAMPLE 5 | 0.998 | 400 | 120 | OK | OBSERVED | 0.03 |
|  | 0.998 | 500 | 120 | OK | NOT OBSERVED | 0.03 |
|  | 0.998 | 600 | 120 | OK | NOT OBSERVED | 0.02 |
|  | 0.998 | 700 | 120 | OK | NOT OBSERVED | 0.01 |
|  | 0.998 | 750 | 120 | OK | NOT OBSERVED | 0.03 |
|  | 0.998 | 900 | 120 | OK | NOT OBSERVED | 0.02 |
| EXAMPLE 6 | 0.995 | 700 | 10 | OK | OBSERVED | 0.02 |
|  | 0.995 | 700 | 15 | OK | NOT OBSERVED | 0.03 |
|  | 0.995 | 700 | 60 | OK | NOT OBSERVED | 0.03 |
|  | 0.995 | 700 | 120 | OK | NOT OBSERVED | 0.01 |
|  | 0.995 | 700 | 240 | OK | NOT OBSERVED | 0.02 |
|  | 0.995 | 700 | 600 | OK | NOT OBSERVED | 0.03 |

US 8,795,491 B2

METHOD OF PROCESSING SENSOR ELEMENT AND SENSOR ELEMENT

BACKGROUND OF THE INVENTION

1. Field of the Invention

The present invention relates to a processing method which improves the characteristics of a NOx sensor, and particularly to a method for improving the followability of a NOx signal relative to a change in a NOx concentration.

2. Description of Related Art

Conventionally, as an apparatus for measuring a NOx concentration in a measurement gas exemplified by a combustion gas or an exhaust gas of an internal combustion engine such as an automobile engine, there has been known a NOx sensor in which a sensor element is formed by using an oxygen-ion conductive solid electrolyte layer such as a zirconia ($ZrO_2$) layer. In this NOx sensor, the concentration of a NOx gas is obtained by utilizing the fact that the amount of oxygen ion generated when a NOx gas is decomposed in a measuring electrode is proportional to a current (also referred to as a NOx signal) flowing in the measuring electrode and a reference electrode.

This NOx sensor is required to have a good responsiveness (followability) to a change in the NOx concentration. For example, it is demanded that, when the NOx concentration in the measurement gas steeply changes, the value of the NOx signal can promptly follow it and change. On the other hand, even when the concentrations of other gas components in the exhaust gas vary, the NOx signal has to be constant unless the NOx concentration varies. Techniques for improving the followability of the NOx signal are already known (see International Publication WO2008/038773, for example).

International Publication WO 2008/038773 discloses that a sensor element constituted of the above-mentioned solid electrolyte and included in a NOx sensor is heated at a temperature of 500° C. or higher and for 15 minutes or longer in an atmosphere containing hydrocarbon (HC) and having an air ratio of 0.80 to 1.10, to thereby resolve an excessive change in an output of a NOx signal.

However, performing a heat treatment on the sensor element in this manner causes the problem that unburned carbon left in the atmosphere adheres to a surface of the element to make the appearance bad, or adversely affects an initial output signal of the sensor element.

SUMMARY OF THE INVENTION

The present invention relates to a processing method for improving the characteristics of a gas sensor, and particularly to a method for improving the followability of a NOx signal relative to a change in a NOx concentration.

According to the present invention, a method of processing a sensor element includes the steps of (a) preparing a gas atmosphere containing hydrocarbon, having an air-fuel ratio of 0.80 to 0.9999, and having a small amount of oxidizing gas added thereto; and (b) subjecting the sensor element to a heat treatment in the gas atmosphere at a temperature of 500° C. or higher for 15 minutes or longer. The sensor element includes an electrochemical pumping cell constituted of an oxygen-ion conductive solid electrolyte and an electrode having a NOx reduction ability. A NOx gas in a measurement gas is reduced or decomposed in the electrode. A NOx concentration in the measurement gas is obtained based on a current which flows in the electrochemical pumping cell at a time of the reduction or decomposition.

According to the present invention, the heat treatment is performed in a rich atmosphere having a small amount of oxidizing gas added thereto, to thereby obtain a good followability of a NOx signal in the sensor element, and additionally prevent occurrence of a bad appearance, an initial output defect, and the like, which may otherwise be caused by unburned carbon deriving from a component of the rich atmosphere.

Therefore, an object of the present invention is to provide a method of processing the sensor element for improving the followability of the NOx signal relative to a change in the NOx concentration, and a method for suitably preventing occurrence of a defect caused by the process.

BRIEF DESCRIPTION OF THE DRAWINGS

FIG. 3 is a diagram plotting the relationship between a NO concentration in an atmosphere in a heat treatment and an excessive output variation value;

FIG. 4 is a diagram showing the followability of the NOx signal with respect to a sensor element obtained by performing a heat treatment by using a furnace including heating means;

FIG. 5 is a diagram showing the followability of the NOx signal with respect to a sensor element obtained by performing a heat treatment on a single body of a sensor element 101 by using a heater 150;

FIG. 6 is a diagram showing the followability of the NOx signal with respect to a sensor element obtained by performing a heat treatment on a gas sensor assembly by using a heater 150; and FIG. 7 is a table showing conditions of heat treatments and evaluation results in experimental examples 4 to 6.

DETAILED DESCRIPTION OF THE INVENTION

<Outline Structure of Gas Sensor>

Figure 1:
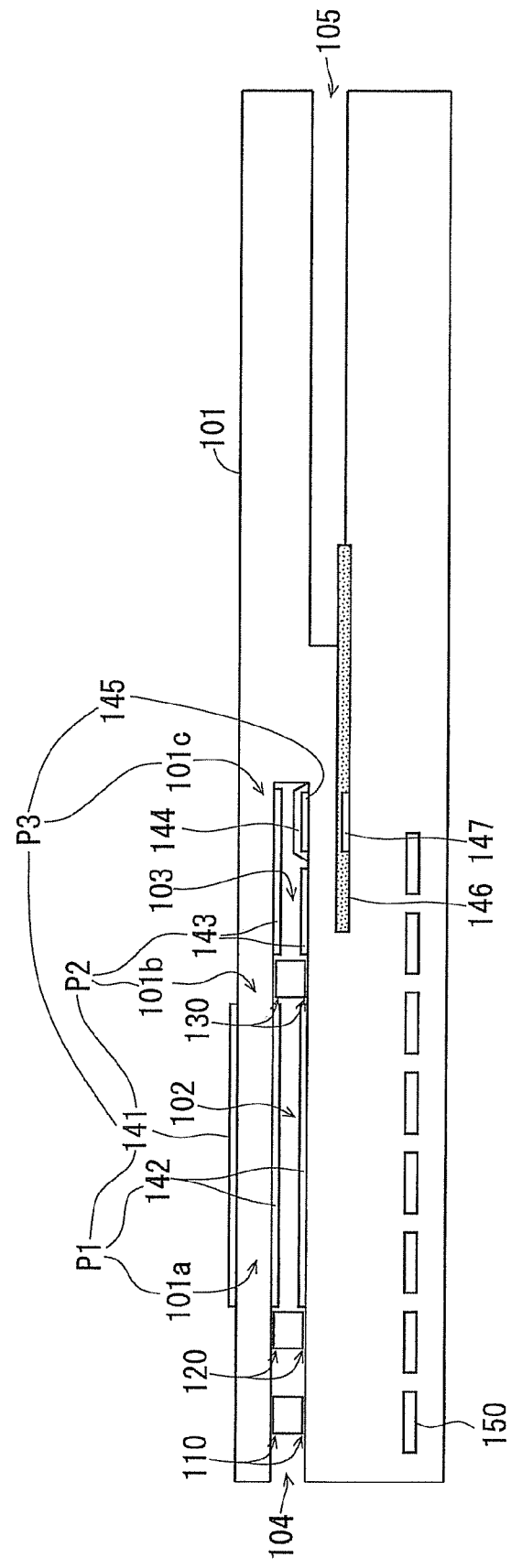
FIG. 1 is a cross-sectional view schematically showing the structure of a sensor element 101 of a NOx sensor to which a processing method according to a preferred embodiment is to be applied.

FIG. 1 is a cross-sectional view schematically showing the structure of a sensor element 101 of a NOx sensor to which a processing method according to this preferred embodiment is to be applied. The sensor element 101 shown in FIG. 1 is a NOx sensor whose structural material is ceramic containing, as a main component, zirconia which is an oxygen-ion conductive solid electrolyte. The structure of the sensor element 101 shown in FIG. 1 is merely illustrative, and a specific structure of the sensor element 101 is not limited thereto.

The sensor element 101 shown in FIG. 1 is a so-called tandem dual-chamber type NOx sensor element in which a first internal space 102 communicates with a gas inlet 104 opened to the outside through a first diffusion control part 110 and a second diffusion control part 120, and a second internal space 103 communicates with the first internal space 102 through a third diffusion control part 130. Calculation of a NOx gas concentration in a measurement gas using this sensor element 101 is performed in the following process.

Firstly, an oxygen concentration of the measurement gas introduced into the first internal space 102 is adjusted to be substantially constant by a pumping operation (pumping in and pumping out of oxygen) of a main pumping cell P1, and then the measurement gas is introduced into the second internal space 103. The main pumping cell P1 is an electrochemical pumping cell constituted by an outside pump electrode 141 provided on an outer surface of the sensor element 101, an inside pump electrode 142 provided in the first internal space 102, and a ceramic layer 101a interposed between these electrodes. In the second internal space 103, oxygen existing in the measurement gas is pumped out by a pumping operation of an auxiliary pumping cell P2 which is also an electrochemical pumping cell, so that the measurement gas is brought into a state of sufficiently low oxygen partial pressure. The auxiliary pumping cell P2 is constituted by the outside pump electrode 141, an auxiliary pump electrode 143 provided in the second internal space 103, and a ceramic layer 101b interposed between these electrodes.

Each of the outside pump electrode 141, the inside pump electrode 142, and the auxiliary pump electrode 143 is formed as a porous cermet electrode (for example, a cermet electrode including Pt containing Au by 1% and zirconia). The inside pump electrode 142 and the auxiliary pump electrode 143 which are brought into contact with the measurement gas are formed using a material having a weakened or no reduction ability with respect to a NOx component in the measurement gas.

NOx in the measurement gas brought into the state of the low oxygen partial pressure by the auxiliary pumping cell is reduced or decomposed in a measuring electrode 145 which is provided in the second internal space 103 so as to be covered with a protective layer 144. The measuring electrode 145 is a porous cermet electrode functioning also as a NOx reducing catalyst which reduces NOx existing in an atmosphere of the second internal space 103. A potential difference between the measuring electrode 145 and a reference electrode 147 is kept constant. The reference electrode 147 is provided within a porous alumina layer 146 communicating with a reference gas inlet 105. Oxygen ion generated by the reduction or the decomposition is pumped out to the outside of the element by a measuring pumping cell P3. The measuring pumping cell P3 is constituted by the outside pump electrode 141, the measuring electrode 145, and a ceramic layer 101c interposed between these electrodes. The measuring pumping cell P3 is an electrochemical pumping cell which pumps out oxygen generated by decomposition of NOx existing in the atmosphere around the measuring electrode 145. In the sensor element 101, a pump current Ip2 which flows between the measuring electrode 145 and the outside pump electrode 141 in accordance with the amount of pumped-out oxygen is detected. In a NOx sensor, a NOx concentration in the measurement gas is obtained based on the fact that there is a linear relationship between a current value (NOx signal) of this pump current Ip2 and a concentration of decomposed NOx.

A heater 150 is provided in the sensor element 101. The heater 150 is provided for heating the sensor element 101 in order to improve the oxygen-ion conductivity of the solid electrolyte during the use of the sensor element 101. The heater 150 is also used in performing a heat treatment which will be described later.

<Improvement of Followability of NOx Signal>

Next, a description will be given of a process which is performed on the sensor element 101 for the purpose of ensuring the followability of the NOx signal to thereby prevent occurrence of an excessive output variation (an overshoot or an undershoot of the NOx signal) when the sensor element 101 is used for measuring a NOx concentration.

Figure 2:
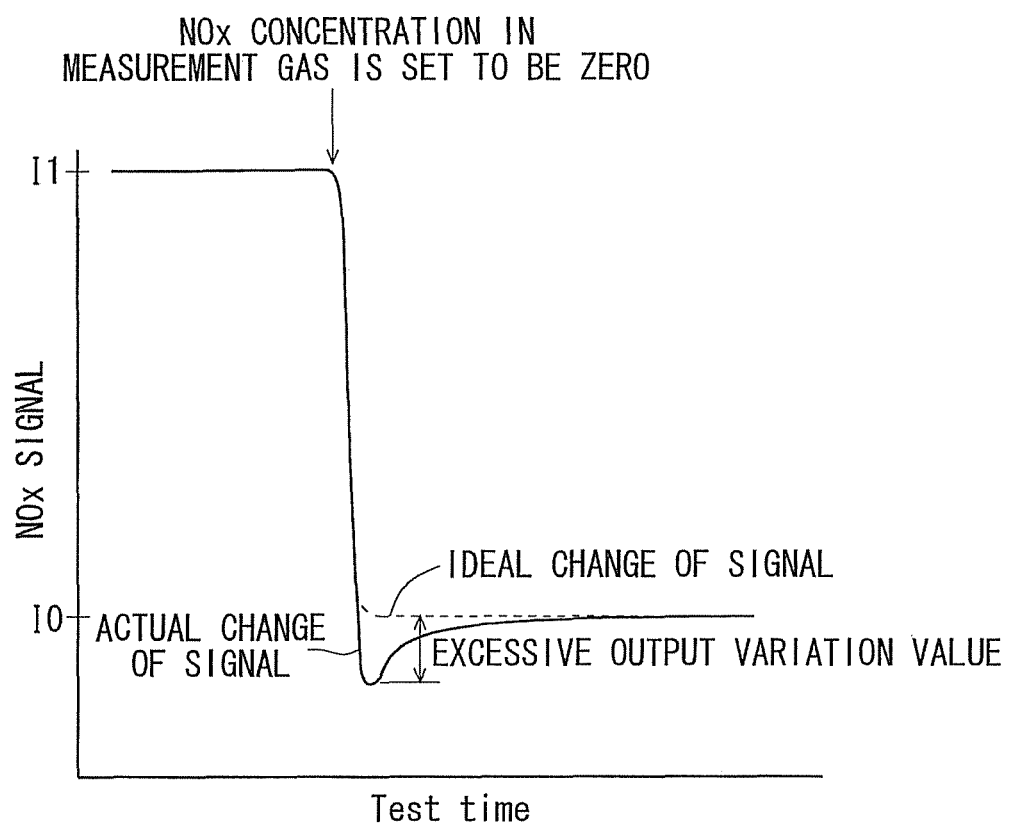
FIG. 2 shows an example of occurrence of an excessive output variation in a NOx signal.

FIG. 2 shows an example of occurrence of an excessive output variation in the NOx signal. In FIG. 2, the solid line and the broken line respectively indicate actual and ideal changes in a NOx signal of a sensor element, in a case where a NOx concentration in a measurement gas suddenly becomes zero while the NOx concentration in the measurement gas is being measured by using the sensor element on which a process for ensuring the followability has not been performed.

If a NOx gas suddenly disappears in a measurement gas containing a predetermined concentration of NOx gas, a NOx signal should, in principle, promptly follow it and change to a corresponding signal value as indicated by the broken line of FIG. 2 (in FIG. 2, the change is I1→I0). However, actually, an excessive output variation not corresponding to the real change in the NOx concentration occurs in the NOx signal, as indicated by the solid line of FIG. 2. In such a case, normally, an undershoot occurs as shown in FIG. 2. Hereinafter, the maximum value of the difference between the ideal value of the NOx signal and the value of the NOx signal obtained when such an output variation occurs will be referred to as an excessive output variation value.

In this preferred embodiment, the above-mentioned excessive output variation is prevented and a good followability of the NOx signal is ensured by heating the sensor element 101 in an atmosphere having an air-fuel ratio of 0.80 to 0.9999 and containing hydrocarbon (HC) and a gas (hereinafter referred to as an oxidizing gas) having an oxidizing property. It is preferable that this heating is performed in an atmosphere having a small amount of oxidizing gas added thereto. That is, this preferred embodiment is characterized by performing the heat treatment in a rich atmosphere containing a small amount of oxidizing gas. When the heat treatment is performed in this atmosphere, a good followability of the NOx signal in the sensor element 101 is obtained, and additionally occurrence of a bad appearance due to unburned carbon, an initial output defect (which means a defect in which a large pump current Ip2 flows in the measuring pumping cell P3 even though no NOx exists), and the like, can be suitably prevented. Heating in an atmosphere having an air-fuel ratio of less than 0.80 is not preferable, because adhering of unburned carbon and an initial output defect occur. When the air-fuel ratio is more than 1.0, the atmosphere becomes a lean atmosphere, and therefore the process in a rich atmosphere which is the feature of this preferred embodiment cannot be performed. In this case, the followability of the NOx signal cannot be obtained and an excessive output variation occurs, which is not preferable. It is more preferable that the air-fuel ratio is 0.9900 to 0.9985. This can ensure the followability of the NOx signal with an enhanced certainty, and additionally can more suitably prevent occurrence of a bad appearance and an initial output defect.

The heat treatment on the sensor element 101 may be performed by forming a rich atmosphere containing a small amount of the oxidizing gas in a chamber (such as a model gas system or a furnace) having heating means, and actuating the heating means while the sensor element 101 is held within the chamber to thereby heat the rich atmosphere in the chamber. Alternatively, the heat treatment may be performed by actuating the heater 150 provided in the sensor element 101 in a space where the similar rich atmosphere is formed. In the latter case, the heating may be performed on a single body of the sensor element 101 before a protective covering (not shown) and the like are assembled thereon so that a gas sensor is formed, or may be performed on a gas sensor assembly (finished product).

As the oxidizing gas, NO, $NO_2$, $N_2O$, $CO_2$, $O_3$, $SO_3$, or the like, may be adopted, and among them NO is preferable. Although CO is sometimes used for forming a rich atmosphere, CO does not exhibit an oxidizing property in the presence of hydrocarbon (such as $C_3H_8$), and therefore a heat treatment in an atmosphere containing CO is not included in the heat treatment in the atmosphere containing an oxidizing gas according to this preferred embodiment.

In a case of using NO, it is preferable that a NO concentration in an atmosphere gas is 0.05% to 1.0%. In this preferred embodiment, any gas concentration is represented as a volume ratio. When the NO concentration is equal to or less than 0.05%, unburned carbon adheres to the sensor element 101, which is not preferable. On the other hand, when the NO concentration is equal to or more than 1.0%, the followability of the NOx signal is not obtained and an excessive output variation occurs, which is not preferable.

Preferably, a heating temperature is 500° C. or higher and a heating time period is 15 minutes or longer. More preferably, the heating temperature is 600 to 750° C. and the heating time period is 1 to 4 hours.

As described above, according to this preferred embodiment, the heat treatment is performed in the rich atmosphere having a small amount of oxidizing gas added thereto, and thereby a good followability of the NOx signal in the sensor element is obtained and additionally occurrence of a bad appearance and an initial output defect due to unburned carbon can be suitably prevented.

EXAMPLES

Experimental Example 1

Seven levels of rich atmosphere gases having different NO concentrations were prepared. The heat treatment was performed on ten sensor element 101 in each of the atmospheres, that is, seventy sensor elements 101 in total. Then, all the sensor elements 101 were inspected for their appearances and evaluated for the followability of a NOx signal.

More specifically, prepared were seven types of atmosphere gases having seven different levels of NO concentrations of 0%, 0.05%, 0.1%, 0.3%, 0.5%, 1.0%, and 1.2%, and having the same $C_3H_6$ concentration of 0.07%. In each of the atmosphere gases, the remainder was $N_2$. The heat treatment was performed on ten sensor elements 101 at 700° C. for two hours in each of the atmospheres. The heating was performed by flowing the atmosphere gas into a furnace in which the ten sensor elements 101 were held, and actuating the heating means provided in the furnace.

After the heat treatment, the sensor elements 101 were inspected for their appearances. Adhering of unburned carbon was observed only in the sensor element 101 heated in the atmosphere having a NO concentration of 0% (that is, the sensor element 101 for which the atmosphere gas containing no oxidizing gas was used). This result indicates that performing the heat treatment in the rich atmosphere having the oxidizing gas added thereto can prevent adhering of unburned carbon.

Experimental Example 2

In this experimental example, for evaluating the followability of a NOx signal relative to an actual variation in the NOx concentration, the sensor element 101 obtained after the heat treatment of the experimental example 1 was attached to an exhaust pipe of a diesel engine having a total displacement of 2000 cc, and the diesel engine was actuated to change the state from a state of the 2000 rpm speed to an idling state. While an operation state of the engine is being changed in this manner, a NOx signal was continuously measured by the sensor element 101, and a change thereof was examined.

FIG. 3 is a diagram plotting the relationship between the NO concentration in the rich atmosphere used for the heat treatment and the excessive output variation value. Each of the black circles represents the average value of the ten sensor elements 101, and the lines above and below each black circle represent the maximum value and the minimum value, respectively.

From the result shown in FIG. 3, it is confirmed that when the amount (concentration) of NO added to the rich atmosphere as the oxidizing gas was 1.0% or less, almost no excessive output variation occurred and a variation among the individual sensor elements 101 was small, whereas when the heat treatment was performed in the atmosphere to which NO was added by 1.2%, an undershoot occurred in each of the sensor elements 101 and a variation among the sensor elements 101 was large. This result indicates that when the amount (concentration) of NO added to the rich atmosphere used for the heat treatment is set to be 1.0% or less, the sensor element 101 stably ensuring its followability relative to a variation in the NOx concentration is obtained.

Experimental Example 3

In this experimental example, the evaluation was made for how a difference in the manner of the heat treatment influences an improvement in the followability of the NOx signal.

More specifically, three sensor elements 101 were prepared. Performed on one of the sensor elements 101 was (a) a heat treatment using a furnace having heating means. Performed on another of the sensor elements 101 was (b) a heat treatment on a single body of the sensor element 101 using the heater 150. Performed on the other of the sensor elements 101 was (c) a heat treatment on the gas sensor assembly using the heater 150. In any of the cases, an atmosphere in the heat treatment was a rich atmosphere containing a NO gas by about 0.13%.

Then, under the same conditions as in the experimental example 2, the three sensor elements 101 subjected to the respective heat treatments were examined for a change in a NOx signal.

FIGS. 4 to 6 are diagrams each showing a change in the NOx signal in the sensor element 101 subjected to each of the heat treatments (a) to (c). FIG. 4 shows a result of the case (a). FIG. 5 shows a result of the case (b). FIG. 6 shows a result of the case (c). In any of FIGS. 4 to 6, also shown in a result of evaluating, under the same condition, a change in the NOx signal in a sensor element 101 not subjected to the heat treatment.

In any of FIGS. 4 to 6, an undershoot occurs in the NOx signal (indicated as "NOT PROCESSED" in FIGS. 4 to 6) of the sensor element 101 not subjected to the heat treatment, whereas no undershoot occurs in the NOx signal (indicated as "PROCESSED" in FIGS. 4 to 6) of the sensor element 101 subjected to the heat treatment.

This result indicates that, irrespective of a specific manner of the heat treatment, performing the heat treatment in a rich atmosphere containing an oxidizing gas can prevent occurrence of an excessive output variation and thus improve the followability of the NOx signal.

Experimental Examples 4 to 6

In experimental examples 4 to 6, evaluations were made for how differences in the air-fuel ratio, the heating temperature, and the heating time period influence the appearance of the element, the followability of the NOx signal, and the initial output. FIG. 7 is a table showing conditions of the heat treatment and evaluation results in the experimental examples 4 to 6.

In the experimental example 4, an influence of the difference in the air-fuel ratio of the atmosphere gas was evaluated. To be specific, atmosphere gases having seven different levels of air-fuel ratios of 0.75, 0.80, 0.90, 0.99, 0.9985, 0.999, and 1.05 were prepared, with the same NO concentration of 0.05% and different $C_3H_6$ concentrations. A process of heating the sensor element 101 at 700° C. for two hours was performed in each of the atmospheres. The heating was performed by flowing each atmosphere gas in a furnace in which the sensor element 101 is held and actuating heating means provided in the furnace.

After the heat treatment, the total seven sensor elements 101 subjected to the heat treatment under the respective conditions were inspected for their appearances. In FIG. 7, "NG" indicates any bad appearance observed in the inspection, and "OK" indicates no bad appearance observed. A change in the NOx signal was measured under the same condition as in the experimental example 2, to evaluate presence or absence of occurrence of an excessive output variation. Additionally, an initial output, that is, the current value of the pump current Ip2 which flows in the measuring pumping cell P3 when NOx does not exist was measured while supplying only an $N_2$ gas as the measurement gas. Although an initial output closer to zero is preferred, a value of the initial output in a range of −0.10 μA to 0.20 μA was accepted as passing the examination in this experimental example.

As a result of these evaluations, as shown in FIG. 7, in a case where the sensor element 101 was subjected to the heat treatment in an atmosphere having an air-fuel ratio of 0.8 to 0.9999, no defect occurred in any of the evaluations. On the other hand, in a case where the sensor element 101 was subjected to the heat treatment in an atmosphere having an air-fuel ratio of 0.75, adhering of unburned carbon and an initial output defect occurred. In a case where the sensor element 101 was subjected to the heat treatment in an atmosphere having an air-fuel ratio of 1.05, an excessive output variation occurred. This result indicates that occurrence of a bad appearance can be prevented and the followability of a NOx signal can be improved by performing the heat treatment in an atmosphere having an air-fuel ratio of 0.8 to 0.9999.

In the experimental example 5, an influence of the difference in the heating temperature was evaluated. To be specific, the sensor element 101 was subjected to the heat treatment at six heating temperatures of 400° C., 500° C., 600° C., 700° C., 750° C., and 900° C. In any of the cases, the atmosphere in the heat treatment was a rich atmosphere having a NO concentration of 0.13%, a $C_3H_6$ concentration of 0.07%, and an air-fuel ratio of 0.998. In any of the cases, the heating time period was two hours. Similarly to the experimental example 4, the heating was performed by flowing an atmosphere gas in a furnace in which the sensor element 101 was held and actuating heating means provided in the furnace.

After the heat treatment, under the same conditions as in the experimental example 4, three types of evaluations were made on the six sensor elements 101 subjected to the respective heat treatments.

As shown in FIG. 7, only when the heating temperature was 400° C., an excessive output variation occurred. When the heating temperature was 500° C. or higher, no defect was observed in any of the evaluations. This result indicates that the effect of improving the followability of a NOx signal by means of the heat treatment cannot be obtained if the heating temperature is too low.

In the experimental example 6, an influence of the difference in the heating time period was evaluated. To be specific, the heat treatment was performed on the sensor element 101 for six types of heating time periods of 10 minutes, 15 minutes, 60 minutes, 120 minutes, 240 minutes, and 600 minutes. In any of the cases, the heating temperature was 700° C. In any of the cases, the atmosphere in the heat treatment was a rich atmosphere having a NO concentration of 0.10%, a $C_3H_6$ concentration of 0.07%, and an air-fuel ratio of 0.995. Similarly to the experimental example 4, the heating was performed by flowing an atmosphere gas in a furnace in which the sensor element 101 was held and actuating heating means provided in the furnace.

After the heat treatment, the six sensor elements 101 subjected to the respective heat treatment were examined for a change in a NOx signal, under the same conditions as in the experimental example 4.

As shown in FIG. 7, only when the heating time period was 10 minutes, an excessive output variation occurred. When the heating time period was 15 minutes or longer, no defect was observed in any of the evaluations. This result indicates that the effect of improving the followability of a NOx signal by means of the heat treatment cannot be obtained if the heating time period is too short.

What is claimed is:

1. A method of processing a sensor element comprising the steps of:
   (a) preparing a gas atmosphere containing hydrocarbon, having an air-fuel ratio of .080 to 0.9999, and having NO as an oxidizing gas added thereto such that a NO concentration is 0.05 or more and less than 1.0% by volume ratio; and
   (b) subjecting said sensor element to a heat treatment in said gas atmosphere at a temperature of 500° C. or higher for 15 minutes or longer,
   wherein said sensor element includes an electrochemical pumping cell constituted of an oxygen-ion conductive solid electrolyte and an electrode having a NOx reducing ability, a NOx gas in a measurement gas is reduced or decomposed in said electrode, and a NOx concentration in said measurement gas is obtained based on a current which flows in said electrochemical pumping cell at a time of said reduction or decomposition.

2. The method according to claim 1, wherein said heat treatment is performed by holding said sensor element in a chamber and in this state heating said gas atmosphere in said chamber by using heating means provided in said chamber.

3. The method according to claim 1, wherein said sensor element includes a heater that is used during operation of said sensor element, and said heat treatment is performed by using said heater.

4. The method according to claim 1, wherein the air-fuel ratio in said gas atmosphere is 0.9900 to 0.9985.

5. The method according to claim 1, wherein the heating temperature in said heat treatment is 600 to 750° C.

6. The method according to claim 1, wherein said electrode is covered with a protective layer.

* * * * *

UNITED STATES PATENT AND TRADEMARK OFFICE
CERTIFICATE OF CORRECTION

PATENT NO. : 8,795,491 B2  
APPLICATION NO. : 13/040621  
DATED : August 5, 2014  
INVENTOR(S) : Tetsuya Ishikawa, Sumiko Horisaka and Yuji Okuda Page 1 of 1

It is certified that error appears in the above-identified patent and that said Letters Patent is hereby corrected as shown below:

In the Claims

Column 8, line 33 (Claim 1)

Please correct: ".080" to -- 0.80 --

Column 8, line 35 (Claim 1)

Please correct: "0.05" to -- 0.05% --

Signed and Sealed this  
Twenty-first Day of October, 2014

Michelle K. Lee  
*Deputy Director of the United States Patent and Trademark Office*